(12) United States Patent
Schacht

(10) Patent No.: US 6,933,328 B2
(45) Date of Patent: Aug. 23, 2005

(54) COMPOSITION OF CROSSLINKABLE PREPOLYMERS FOR BIODEGRADABLE IMPLANTS

(75) Inventor: Etienne Honoré Schacht, Staden (BE)

(73) Assignee: Universiteit Gent, Ghent (BE)

(*) Notice: Subject to any disclaimer, the term of this patent is extended or adjusted under 35 U.S.C. 154(b) by 201 days.

(21) Appl. No.: 10/239,623

(22) PCT Filed: Apr. 3, 2001

(86) PCT No.: PCT/EP01/03766

§ 371 (c)(1),
(2), (4) Date: Jan. 8, 2003

(87) PCT Pub. No.: WO01/74411

PCT Pub. Date: Oct. 11, 2001

(65) Prior Publication Data

US 2003/0114552 A1 Jun. 19, 2003

(30) Foreign Application Priority Data

Apr. 3, 2000 (EP) .......................................... 00201198

(51) Int. Cl.$^7$ .............................. A61F 2/00; A61K 6/08; C08K 3/26; C08K 3/32
(52) U.S. Cl. ...................... 523/115; 523/116; 522/104; 522/135; 524/17; 524/47; 524/414; 524/425; 424/426; 424/601
(58) Field of Search ................................ 523/115, 116; 522/104, 135; 524/17, 47, 414, 425; 424/426, 601

(56) References Cited

U.S. PATENT DOCUMENTS

| | | | |
|---|---|---|---|
| 5,085,861 A | * | 2/1992 | Gerhart et al. ........... 424/78.17 |
| 5,108,755 A | | 4/1992 | Daniels |
| 5,278,202 A | | 1/1994 | Dunn |
| 5,410,016 A | | 4/1995 | Hubbell |
| 5,717,030 A | | 2/1998 | Dunn . |
| 5,837,752 A | | 11/1998 | Shastri |
| 5,900,245 A | | 5/1999 | Sauhney et al. |
| 6,171,610 B1 | | 1/2001 | Vacanti et al. |
| 6,177,095 B1 | | 1/2001 | Sawhney et al. |
| 6,207,749 B1 | | 3/2001 | Mayes |
| 6,352,710 B2 | | 3/2002 | Sawhney |

FOREIGN PATENT DOCUMENTS

| | | |
|---|---|---|
| EP | 0 795 573 A2 | 9/1997 |
| WO | WO 00/44808 A1 | 8/2000 |
| WO | WO 01/91822 A1 | 12/2001 |

* cited by examiner

*Primary Examiner*—Tae H. Yoon
(74) *Attorney, Agent, or Firm*—Barnes & Thornburg

(57) ABSTRACT

A composition suitable for preparing a biodegradable implant, comprising a crosslinkable multifunctional prepolymer having at least two polymerizable end groups, the said composition having a viscosity such that it is deformable at a temperature of 0° to 60° C. into a three-dimensional shape and being crosslinkable within the said temperature range. The prepolymer comprises a hydrophilic region and/or the composition further comprises an effective amount of a mineral biologically-active component delivery system and/or a biocompatible degradable porosity-inducing component.

21 Claims, 4 Drawing Sheets

COMPOSITION OF CROSSLINKABLE PREPOLYMERS FOR BIODEGRADABLE IMPLANTS

The present invention is in the field of therapeutically active biodegradable implants. More specifically, the invention relates to crosslinkable polyester, polyorthoester or polyacetal prepolymers for use in the manufacture of such implants, as well as to specific biologically-active crosslinkable prepolymer formulations and to implants obtained by crosslinking such formulations. The present invention further refers to a method for repairing bone defects and to a method for the fixation of a dental implant in a mammal while making use of these prepolymers and formulations.

BACKGROUND OF THE INVENTION

Biodegradable polymers are widely used nowadays and have been designed for a broad range of medical applications and devices like implants in order to fulfill a temporarily mechanical function, such as for bone plates, sutures and the like and/or to deliver a drug locally in a controlled manner. In such applications, an implant material with an appropriate strength is required in order to provide a temporarily bridge in the bone defect.

In particular with respect to mechanical medical devices, a method is already known whereby cells having a desired function are grown on a prefabricated polymer scaffold, followed by transfer of the cell-polymer scaffold into a patient at a site appropriate for attachment in order to produce a functional organ equivalent. Success of this procedure mostly depends on the ability of the implanted cells to attach to the surrounding environment and to stimulate angiogenesis. The polymer scaffolding used for the initial cell culture is made of a material which degrades over time and is therefore no longer present in the chimeric organ. The preferred material for forming the matrix structure usually is a biodegradable synthetic polymer such as polyglycolic acid, polyorthoester, polyanhydride or the like, which is easily degraded by hydrolysis. This material may be overlaid with a second material such as gelatine or agarose in order to enhance cell attachment. In the case of making a cartilageneous structure, such a procedure is described namely in U.S. Pat. No. 5,041,138 making specific mention of polyglactin, a 90:10 copolymer of glycolide and lactide marketed by Ethicon Co. (Somerville, N.J.) under the trade name Vicryl®. The polymer matrix must provide an adequate site for attachment and adequate diffusion of nutrients and/or growth factors supplied during cell culture in order to maintain cell viability and growth until the matrix is implanted and vascularization has occurred. A preferred structure for organ construction therefore is a structure formed of polymer fibres having a high surface area which results in a relatively low concentration gradient of nutrients to achieve uniform cell growth and proliferation. Examples of such a technology are provided in EP-A-795,573 and U.S. Pat. No. 5,108,755. The latter discloses an implantable reinforcement device exhibiting relatively high stiffness, based on a substrate polymer selected from poly(orthoester), polylactic acid, polyglycolic acid and polycaprolactone, showing initial flexural strength and modulus (according to ASTM D 790-81) of 65 MPa and 1.6 GPa respectively. The said device retained 90% of its initial flexural strength and modulus at 6 weeks in vitro, but radiation sterilization reduced initial flexural strength by 60% and increased the degradation rate, thus severely compromising mechanical properties. Obviously a disadvantage of this kind of method is that the shape of the prefabricated polymer scaffold can hardly be changed at the time of implanting it into the patient.

In view of providing an implant, optionally with a drug system, into the body without incision, while avoiding the disadvantages of injected microparticles (which do not form a continuous film or implant with the structural integrity needed, and cannot be removed without extensive surgery if complication occurs), U.S. Pat. No. 5,278,202 discloses an injectable composition suitable for in situ implant within the living body, e.g. bone or the periodontal cavity, without the use of solvents, comprising:

(a) a pharmaceutically acceptable liquid acrylic ester-capped prepolymer formed from a low molecular weight oligomer having terminal functional groups able to react with acryloyl chloride,
(b) a pharmaceutically acceptable curing agent, and
(c) optionally a biologically active agent such as peptide and protein drugs.

U.S. Pat. No. 5,837,752 also discloses a composition in a form suitable for bone repair or replacement, bone cement or dental material. Following exposure to active species (such as photo-initiators or thermal initiators), it forms a solid semi-interpenetrating polymer network (i.e. a composition of two independent components being a crosslinked polymer and a non-crosslinked polymer), capable of supporting bone growth and repair, comprising:

(a) a linear hydrophobic biodegradable polymer,
(b) a monomer or macromer including a degradable anhydride linkage and containing a free radical (meth)acrylate polymerizable group, and
(c) optionally a reactive or non-reactive viscosity modifier,
(d) optionally therapeutic and/or diagnostic agents, and
(e) optionally porosity forming agents, including inorganic salts and proteinaceous materials with a particle size 100–250 $\mu$m.

The said composition can have a viscosity before crosslinking ranging from a viscous liquid suitable for injection to a moldable paste-like putty. Examples of hydrophobic polymers (a) include polyorthoesters, polydioxanones, polycarbonates, polyaminocarbonates, polyhydroxyacids and polyanhydrides. The only illustrated embodiment deals with network copolymerizing the methacrylic anhydrides of sebacic acid and 1,3-bis(p-carboxy phenoxy)propane. This composition has the disadvantage that therapeutic agents having a hydroxy or amine functionality reactive with the anhydride linkage must be incorporated indirectly, i.e. in the form of microparticles.

Among biodegradable polymers, special attention has been paid to polyesters and copolyesters, especially those based on lactones such as $\epsilon$-caprolactone, glycolide and lactides. In particular, the controlled release of bioactive agents from lactide/glycolide polymers is described in U.S. Pat. No. 3,773,919. Also, U.S. Pat. No. 4,902,515 discloses encapsulating a biologically active ingredient in interlocked segments of poly(R-lactide) and poly(S-lactide).

Suitable polymer implants, in particular polyester implants, can be conventionally prepared while using biodegradable polymeric compositions obtained by solvent casting, filament drawing, meshing, extrusion-molding or compression-molding. Therapeutically active implants can similarly be prepared by dispersing a drug into a polymer matrix and then extruding the resulting mixture. Due to the usually high temperatures necessary for extruding polymers, such a procedure is obviously mainly limited to biologically active drugs with a substantially high thermal stability. This procedure is therefore not easily applicable to thermally degradable drugs such as most peptides and proteins. In many cases, the active forms of proteins are difficult to formulate together with biodegradable polymers.

For tailoring a biological material to the specific physicochemical requirements encountered when a synthetic load-bearing (e.g. a hip) or non load-bearing (e.g. a cronal fracture) therapeutically active biodegradable bone implant is to be hardened in situ at the place where bone growth is expected, numerous factors have to be taken into account. First, when a degrading polymer matrix comprises a sequence, such as a polyester or a polyorthoester, which is able to generate acidic compounds such as lactic acid or glycolic acid, the growing medium for bone forming cells such as osteoblasts becomes too acidic and constitutes an unfavourable environment for bone reconstruction. Therefore there is a need in the art for an in situ implantable biological material suitable for bone reconstruction and which overcomes the problem of acidic polymer matrices, in particular a composition able to provide a slightly alkaline medium in the implant, thus favouring interaction with osteoblasts. Secondly, there is also a need in the art for injectable compositions suitable for in situ implant within the living body, based on liquid capped prepolymers, which are able to degrade more quickly. Thirdly there is also a need for biodegradable in situ implantable compositions, the leaching time of which can be better spread or controlled, for instance wherein the active-ingredient does not leach out of the matrix before the said polymer matrix degrades. Consequently, as a general rule, there is a need for the design of specific biocompatible crosslinkable polymer formulations, which are able to meet specific requirements for use as implant materials for the healing of bone defects or in the fixation of dental implants.

SUMMARY OF THE INVENTION

The present invention is based on the discovery that the above-mentioned difficulties in using biodegradable polymers for effectively repairing bone defects in mammals, especially in humans, horses, dogs, bovines and the like, can be overcome by a proper selection of the formulation components in order to meet both the physico-chemical, in particular viscosity, pH and degradability, requirements of medical procedures such as the in situ bone implant technology and the compatibility with a wide range of biologically active additives which may most often be used in order to improve the chances of success of such procedures. Therefore, in a first aspect, the present invention provides a composition suitable for preparing a biodegradable implant, comprising a crosslinkable multifunctional prepolymer having at least two polymerizable end groups, the said composition having a viscosity such that it is deformable at a temperature of about 0° to 60° C. into a three-dimensional shape and being crosslinkable within the said temperature range, characterized in that the said crosslinkable multifunctional prepolymer comprises a hydrophilic region, the said crosslinkable multifunctional prepolymer preferably comprising at least one of a polyester, a polyorthoester or a polyacetal, and the said composition being suitable for the preparation of a therapeutically-active biodegradable implant, especially for in situ bone repair or dental application. In a second aspect, the present invention provides a composition suitable for preparing a biodegradable implant, comprising a crosslinkable multifunctional prepolymer having at least two polymerizable end groups, the said composition having a viscosity such that it is deformable at a temperature of about 0° to 60° C. into a three-dimensional shape and being crosslinkable within the said temperature range, wherein the said composition further comprises an effective amount of a mineral biologically-active component delivery system, preferably a mineral system of a nature and in an amount which is able to increase the pH within the degrading polymer matrix and consequently to favour interaction with surrounding cells such as osteoblasts. In this second embodiment, the prepolymer preferably is an acid-generating degrading matrix such as a polyester sequence (for instance prepared from a mixture of lactones in suitable amounts) or a polyorthoester. In a third aspect, the present invention further provides a composition suitable for preparing a biodegradable implant, comprising a crosslinkable multifunctional prepolymer having at least two polymerizable end groups, the said composition having a viscosity such that it is deformable at a temperature of about 0° to 60° C. into a three-dimensional shape and being crosslinkable within the said temperature range, wherein the said composition further comprises an effective amount of a biocompatible degradable porosity-inducing component which, among others, may be a polysaccharide or a chemically-modified derivative thereof such as a crosslinked gelatine. The invention also relates to the use of the aforesaid compositions for the preparation of a therapeutically active implant, for instance a bone implant or a bone cement, or for the fixation of a dental material. In another aspect, the present invention provides a method for repairing a bone defect by implanting a bone repair low viscosity formulation based on the said biodegradable multifunctional crosslinkable prepolymer or macromer into the body of a mammal, namely a human, a horse, a dog, a bovine or the like, at a place suitable for bone growth and further crosslinking the said formulation by suitable means such as light and/or moderate temperature until hardening takes place.

DETAILED DESCRIPTION OF THE INVENTION

Figure 1:
FIG. 1 represents the histograph of a composite comprising gelatine and a crosslinked biodegradable polymer implanted in cranal defects of a dog.
Figure 2:
FIG. 2 represents the histograph of a composite comprising a crosslinked biodegradable polymer implanted in cranal defects of a dog without gelatine.

The present invention will be described with reference to certain embodiments but the invention is not limited thereto but only by the appended claims.

The present invention is based on the unexpected discovery that the aforesaid problems, namely of medium acidity, rate of pore formation and speed of degradability, of the known crosslinkable multifunctional prepolymers having at least two polymerizable end groups (hereinafter also referred to as a "macromer"), for instance based on a polyester or a polyorthoester, can be satisfactorily solved by properly modifying them through the introduction of a hydrophilic sequence or by properly formulating them with at least one biologically-active substance such as a ligand, a peptide or a protein (including a bone morphogenetic protein or a transforming growth factor), optionally chemically modified in order to contain polymerizable groups, and/or with a mineral delivery system. Macromers suitable for performing the present invention may be designed in a number of different ways, as will be further explained below, provided that they contribute in a biodegradable composition that, due to its desirable viscosity, can be easily implanted and hardened at a moderate temperature into the body of a mammal, i.e. preferably applied to a bone component of a mammal and more preferably poured or injection-molded into a bone cavity of a mammal such as a human, a horse, a dog, a bovine or the like. These different ways of achieving the desired result may be combined in the design of a macromer of the invention, if necessary.

The term macromer as used herein, unless otherwise stated, means a multicomponent prepolymer comprising (1) at least one biodegradable region and (2) at least one, preferably two or more, polymerizable region(s) and optionally (3) a hydrophilic region. Preferably, the biodegradable region of the macromer is biocompatible and forms the central core or backbone to which is (are) attached one or, more preferably, at least two polymerizable region(s) consisting of polymerizable end groups. The macromer may be polymerized to form a network which can be formulated with suitable additives for successful implantation into the body of a mammal, preferably a human. Preferably in the macromer of the invention, the polymerizable regions are separated by at least one biodegradable region in order to facilitate uniform degradation in vivo. The macromers used in the present invention may be constructed in various ways. For instance, in a preferred embodiment, a central hydrophilic region has at least two biodegradable regions attached to it with at least two polymerizable regions attached to the said biodegradable regions so that, upon degradation, the polymerizable regions in their polymerized gel form become separated. Furthermore, in each mode of construction, the number of biodegradable regions and/or polymerizable regions and/or hydrophilic regions is not limited to two but may be three, four or even more, thus resulting in branched, grafted, star-shaped and/or comb-shaped structures.

In order to obtain a biodegradable material with a viscosity suitable for the manufacture of implants, such as specified hereinbefore, it is most preferred that the average number molecular weight of the crosslinkable macromer of this invention (as determined by gel permeation chromatography according to standards and procedures well established in the art) be in the range of about 150 to about 20,000, preferably from about 2,000 to 6,000 and more preferably from about 2,500 to 5,000. If necessary, the viscosity of the biodegradable material may however be adjusted by formulating the crosslinkable macromer with a suitable amount of a viscosity regulator such as a monomer, as explained hereinafter.

The chemical constitution of each component of the macromer such as above-defined will now be explained in further details.

One of the building components for the preparation of a prepolymer with a hydrophilic region may be a polyether polyol with two or more hydroxyl groups derived from polyethylene glycol or a copolymer of ethylene oxide and an alkylene oxide (e.g. propylene oxide) with a degree of polymerization in the range of 2 to about 500. For instance the sequence forming the hydrophilic regions may be represented by the formula —O—R—O—, wherein R may be an alkylene group possibly substituted with one or more hydroxy groups or alternatively R may be

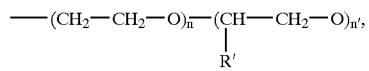

wherein R' is methyl or a higher order alkyl chain and n is from 1 to about 200, more preferably 1 to 10 and n' is 0 to about 100, preferably 0 to 20.

Examples of polyol intitiators suitable for the preparation of the prepolymer of the present invention include for instance low molecular weight polyols (i.e. having a molecular weight of not more than about 300, preferably not more than 150) such as e.g. ethylenediol, propanetriol (glycerol), butanediol-1,4 (tetramethyleneglycol), propanediol-1,3 (trimethylene-glycol), pentanediol-1,5 (penta-methyleneglycol), hexanediol-1,6, diethyleneglycol, triethyleneglycol, tetraethyleneglycol, pentaerythritol, propylene glycol, pentaerythritol, dipentaerythritol and the like. As will readily be understood by those skilled in the art, the above list should not be considered as limiting the scope of the invention. Preferably when the biodegradable region of the macromer used in the present invention is suitably selected as a predominantly amorphous region, as explained hereinafter, then the polyol initiatior for the preparation of the prepolymer of the present invention may be a medium or high molecular weight polyol sequence, i.e. a polyol sequence having a molecular weight of at least about 400 and up to about 10,000.

As is well known to those skilled in the art, a suitable polymer sequence for the biodegradable region of the macromer of the present invention may be a poly-α-hydroxyacid, a polyester sequence (e.g. a polylactone), a polyester sequence (e.g. a polyactone), a polyaminoacid, a polyanhydride, a polyorthoester, or a mixture of these polymers. It may also be a polyacetal sequence. A first class of preferred biodegradable polymer sequence consists of polymers and copolymers (whether random, block, segmented or grafted) of lactones such as ε-caprolactone, glycolide, L-lactide, D-lactide, meso-lactide, 1,4-dioxan-2-one, trimethylene carbonate (1,3-dioxan-2-one), χ-butyrolactone, δ-valerolactone, 1,5-dioxepan-2-one, 1,4-dioxepan-2-one, 3-methyl-1,4-dioxan-2,5-dione, 3,3 diethyl-1,4-dioxan-2,5-one, ε-decalactone, pivalolactone and 4,4-dimethyl-1,3-dioxan-2-one and the like. Several embodiments of such copolymers have been described by, among others, U.S. Pat. Nos. 5,951,997, 5,854,383 and 5,703,200 and shall be considered as being within the scope of the present invention. Particularly preferred for carrying out this invention are non-crystalline, low crystallinity or predominantly amorphous lactone copolymers, especially copolymers of two or more lactones wherein none of the lactone comonomers is present in the resulting copolymer in a molar proportion above 75%, more preferably above about 70%. As usual, crystallinity for the purpose of this embodiment of the invention shall be measured by X-ray diffractometry, while using test methods and apparatus well known in the art. The terms "low crystallinity" or "predominantly amorphous" as used herein, unless otherwise stated, shall mean a degree of crystallinity not exceeding about 50%, preferably not exceeding 15% and more preferably not exceeding 5%.

A second class of preferred biodegradable polymer sequence for the macromer of the invention consists of hydroxy-terminated polyorthoesters obtainable for instance by the addition reaction of a diol (e.g. an alkylenediol such as ethylenediol, trimethyleneglycol, tetramethyleneglycol, pentamethyleneglycol, hexanediol-1,6 and the like, or a cycloalkyldiol such as 1,4-cyclohexanedimethanol or 1,4- cyclohexanediol) or polyethyleneglycol onto a diketene acetal. Such a method for a hydroxy-terminated polyorthoester is well known in the art and is described, starting from 3,9-bis(ethylidene-2,4,8,10-tetraoxaspiro[5,5]undecane, by J. Heller et al. in *Macromolecular Synthesis* 11:23–25.

Yet another class of preferred biodegradable polymer sequence for the macromer of the invention consists of hydroxy-terminated polyacetals obtainable for instance by the condensation reaction of at least a diol (such as hereinabove mentioned) and a divinylether, as is well known in the art. For instance, U.S. Pat. No. 4,713,441 describes unsaturated, linear, water-soluble polyacetals having molecular weights from about 5,000 to about 30,000 which may be formed by condensing a divinylether, a water-soluble polyglycol and a diol having a (preferably pendant) unsaturation, which may be further converted to hydrogels, for instance by using a free-radical initiator in order to copolymerize the double bonds in the polyacetal with a monomeric compound having a reactive double bond. Another typical procedure for this kind of polyacetals may be found in Heller et al., *Journal of Polym. Science, Polym. Letters Edition* (1980) 18:293–7, starting from 1,4-divinyloxybutane or diethyleneglycol divinylether. French patent No. 2,336,936 further refers to crosslinked polyacetals formed by condensing diols or polyols with 3,4-dihydro-2H-pyran-2-ylmethyl-3,4-dihydro-2H-pyran-2-ylcarboxylate.

One way of obtention of polyacetals useful within the scope of the present invention may be generalized as follows:

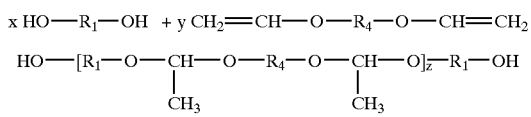

wherein $R_1$ is a sequence of 2 to 20 methylene units and $R_4$ is a sequence of 2 to 20 methylene units or is represented by the formula

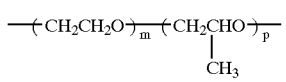

wherein each of m and p is from 0 to 1,000 provided that m+p is from 1 to 1,000.

An alternative method for obtaining polyacetals useful within the scope of the present invention is for instance as follows:

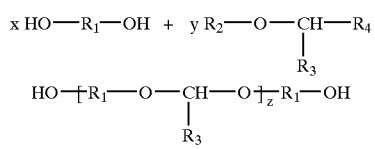

wherein $R_1$ is a sequence of 2 to 20 methylene units and each of $R_2$ and $R_3$ independently represents an alkyl or alkylaryl group and x>y, the ratio x/y determining the polymerization degree z.

The polymerizable region(s) of the crosslinkable multifunctional prepolymer of the invention contain polymerizable end groups such as ethylenic and/or acetylenic unsaturations capable of polymerizing the said macromer, optionally together with other unsaturated monomers which may be present in the composition, under suitable conditions as decribed hereinafter. The choice of suitable polymerizable groups will be dictated by the need for rapid polymerization and gelation. Therefore, namely because they can easily be polymerized while using various polymerization initiating systems, as discussed below, acrylate, methacrylate, acrylamide and methacrylamide groups are preferred.

The crosslinkable multifunctional prepolymers of the invention can be produced by various methods. A first method will be explained by reference to macromers based on polylactones and comprises polymerizing a lactone or, preferably, copolymerizing a mixture of lactones wherein none of the lactones is present in a molar proportion above 75%, at a temperature between about 120° C. and 180° C. in the presence of at least a polyol preferably being in a controlled molar excess with respect to the said mixture of lactones, and further in the presence of at least a lactone polymerization catalyst, for instance a transition metal carboxylate such as zinc diacetate or tin dioctoate. Such a method is able to provide random copolymers as well as copolymers comprising block sequences, depending on the comonomer composition and ratio as well as on the operating conditions, as is well known to those skilled in the art. For the purpose of the present invention, it is usually preferable that the polyol(s) be used in a molar ratio, with respect to the lactone(s), of not more than about 1:10, more preferably not more than about 1:20. After copolymerization, and possibly after removal of the polymerization catalyst from the polyester diol obtained, the latter is further reacted with a monomer containing at least an ethylenic (or acetylenic) unsaturation such as a vinyl group, for instance an acrylic monomer. The said monomer may be any acrylic monomer reactive with the terminal hydroxy groups of the polyester diol, such as acrylic or methacrylic acid (the molar ratio acrylic:polyester then being at least 2) or methacrylic anhydride (the molar ratio acrylic:polyester then being at least 1). This acrylation step may be carried out in the presence of a suitable solvent such as methylene chloride and optionally at least one catalyst, e.g. a tertiary amine such as 4,N-dimethylaminopyridine, triethylamine or the like.

Another method for preparing crosslinkable multifunctional prepolymers of the invention involves anionically polymerizing a lactone or, preferably, copolymerizing a mixture of lactones wherein none of the lactones is present in a molar proportion above 75%, at a temperature below about 30° C. in the presence of an aprotic solvent, e.g. tetrahydrofuran or the like, and further in the presence of an anionic polymerization catalyst such as an alcaline metal alkoxide of a tertiary alcohol (e.g. sodium, potassium or cesium tertiary butoxide) and/or a crown-ether such as 1,4,7,10,13,16-hexaoxocyclooctane (18 crown-6). As is well known in the art, such a polymerization method can take place at very low temperatures, i.e. down to about −78° C. Preferred alcaline metal alkoxides as co-reactants with the lactone(s) include sodium and potassium methoxylates. During or after polymerization, a monomer containing at least one ethylenic (or acetylenic) unsaturation such as a vinyl group, e.g. an acrylic monomer (such as above defined), is added to the reaction mixture in order to perform the final step, preferably an acrylation step, leading to formation of the crosslinkable macromer.

Yet another method for preparing a crosslinkable multifunctional polyorthoester prepolymer of the invention comprises polymerizing at least a diketene acetal in the presence of at least one polyol, the alcohol groups preferably being in a molar excess with respect to the ketene acetal groups, and of at least a diketene acetal polymerization catalyst and, optionally after removal of the catalyst from the (co)polymer obtained, reacting the hydroxyl end groups of the latter with a monomer containing at least an ethylenic (or acetylenic) unsaturation, e.g. a vinyl group such as an acrylic monomer (as defined hereinabove).

Yet another method for preparing a crosslinkable multifunctional polyacetal prepolymer of the invention comprises (co)polymerizing at least a divinylether derivative in the presence of at least one polyol, the alcohol groups preferably being in a molar excess with respect to the vinylether groups, and of at least a vinylether polymerization catalyst and, optionally after removal of the catalyst from the polymer obtained, reacting the hydroxyl end groups of the latter with a monomer containing at least one ethylenic (or acetylenic) unsaturation, for instance a vinyl group, such as an acrylic monomer (as defined hereinabove). Alike in the previous embodiment, it is preferred that the molar ratio of alcohol groups (originating from the polyol) to the ketene acetal or vinylether is in a controlled excess of between about 0.1% and 30%, more preferably from 1% to 5%.

Methods for attaching the polymerizable region(s) to the degradable region(s) of the crosslinkable macromer of the invention are conventional in the art. In addition to the embodiments described hereinabove, mention may be made of attaching an acrylamide or a methacrylamide end group by reacting the terminal hydroxy groups of a biodegradable polymeric sequence, such as a polyacetal, with at least an unsaturated azlactone, preferably a 2-alkenyl azlactone. The term "azlactone" as used herein, unless otherwise stated, means an α-acylaminoacid anhydride such as for instance containing the 2-oxazolin-5-one or the 2-oxazin-6-one functional unit. Most preferred 2-alkenyl azlactones include these wherein the alkenyl group has from 2 to 20 carbon atoms, in particular:

vinylazlactones such as 2-vinyl-4,4-dimethyl-2-oxalin-5-one (available from SNPE, Inc., Princeton, N.J.) represented by the following formula:

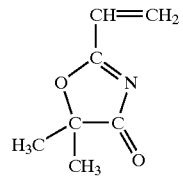

2-isopropenyl-4,4-dimethyl-2-oxalin-5-one, 2-vinyl-4-ethyl-4-methyl-2-oxalin-5-one and the like such as disclosed in U.S. Pat. No. 4,305,705.

The azlactone heterocycle is highly reactive with hydroxy nucleophiles and will therefore provide the unsaturated amide group under suitable reaction conditions.

Thanks to any of the above embodiments, e.g. by selecting a mixture of lactones for achieving an amorphous biodegradable region and/or by selecting a molar ratio polyol(s):lactone(s) of not more than about 1:100, preferably 1:10 and/or by selecting a biodegradable polyacetal sequence, it becomes possible to obtain a composition having a suitable viscosity which is useful for the manufacture of a therapeutically-active biodegradable implant.

The present invention provides biologically-active formulations based on the above described crosslinkable macromers in admixture with biocompatible additives suitable for the intended therapeutic use, in particular for the preparation of load-bearing and non load-bearing in situ hardenable implants. In particular, this invention provides incorporating one or more medico-surgically useful substances into said formulations, in particular those which are able to accelerate or beneficially modify the healing process when the formulations are applied in vivo at a bone repair site. For example, the formulations of this invention include at least one biologically-active component, preferably in a biologically effective amount, such as a therapeutic, diagnostic or prophylactic agent. The therapeutic agent can be selected for its antimicrobial properties, ability to promote bone repair or reconstruction and for specific indications such as thrombosis. These include for instance antimicrobial agents such as broad spectrum antibiotics for combating clinical and sub-clinical infections at the bone repair site, for example gentamycin, vancomycine and the like. Other suitable therapeutic agents include naturally occurring or synthetic organic or inorganic compounds well known in the art, including proteins and peptides (produced either by isolation from natural sources or recombinantly), hormones, bone repair promoters, carbohydrates, antineoplastic agents, antiangiogenic agents, vasoactive agents, anticoagulants, immunomodulators, cytotoxic agents, antiviral agents, antibodies, neurotransmitters, oligonucleotides, lipids, plasmids, DNA and the like. More specifically, suitable bone repair promoters include bone growth factors, bone morphogenetic proteins, transforming growth factors and the like. Suitable therapeutically active proteins include fibroblast growth factors, epidermal growth factors, platelet-derived growth factors, macrophage-derived growth factors such as granulocyte macrophage colony stimulating factors, ciliary neurotrophic factors, cystic fibrosis regulator genes, tissue plasminogen activator, B cell stimulating factors, cartilage induction factor, differentiating factors, growth hormone releasing factors, human growth hormone, hepatocyte growth factors, immunoglobulins, insulin-like growth factors, interleukins, cytokines, interferons, tumor necrosis factors, nerve growth factors, endothelial growth factors, non-steroidal anti-inflammatory drugs, osteogenic factor extract, T cell growth factors, tumor growth inhibitors, enzymes and the like, as well as fragments thereof.

Suitable diagnostic agents include conventional imaging agents (e.g. as used in tomography, fluoroscopy, magnetic resonance imaging and the like) such as transition metal chelates. Such agents will be incorporated into the formulations of the invention in an effective amount for performing the relevant diagnostic.

According to one embodiment, in view of controlling the pH of the medium (namely in the presence of a prepolymer sequence able to generate acidic compounds upon degradation) and/or favouring interaction with osteoblasts, the compositions of this invention include a mineral biologically-active component delivery system of a nature and in an amount suitable for the manufacture of an implant, in particular a bone implant, such as for instance demineralized bone powder, hydroxyapatite powder or particles, coral powder, resorbable calcium phosphate particles, α-tricalcium phosphate, octacalcium phosphate, calcium carbonate, calcium sulfate and the like. Preferably the weight ratio mineral system:prepolymer is in the range from 0.05:1 to 20:1, more preferably in the range from 0.25:1 to 1.6:1.

According to another embodiment, the compositions of this invention include an effective amount of at least a degradable biocompatible porosity-inducing, preferably network-forming, component (or porosigen), such as a porous gelatine (preferably with a particle size from about 50 to 300 μm) or a carbohydrate such as a monosaccharide, an oligosaccharide (e.g. lactose), a polysaccharide (e.g. a polyglucoside such as dextrane), a gelatine derivative containing polymerizable side groups (in the latter case, the formation of an interpenetrating network with the macromer becomes possible) or porous polymeric particles. The latter may be made for instance from acrylic copolymers comprising e.g. one or more alkyl methacrylates, 2-hydroxyethyl methacrylate and possibly acids such as acrylic acid, methacrylic acid, vinylphosphonic acid, crotonic acid and the like). While inducing porosity and controlling the rate of pore formation, these additives will stimulate angiogenesis. By complexing calcium ions, they are also able to promote calcium phosphate deposition and hence bone formation. An effective amount of the porosigen component is such that the weight ratio porosigen:prepolymer is in the range from 0.05:1 to 20:1, more preferably in the range from 0.25:1 to 1.5:1.

The biologically-active component of this invention may be a ligand with affinity for surrounding cells (such as mesenchymal cells) or a chemically modified derivative thereof. More specifically, the said ligand may be a sequence, a fragment or a derivative of a natural extracellular matrix protein like fibronectin or vitronectin which is able to mediate adhesion of cells to each other and to their surroundings and to transduce signals across the cell membrane, via binding and releasing integrins, thus leading to changes in gene expression, cell behavior and differentiation. Fibronectin is a glycoprotein which may be found in the extracellular matrix (where it is in the form of insoluble fibrils) and in blood plasma (as a soluble dimer) and which can mediate interactions between cells and extracellular matrix. Fibronectin can also bind to other matrix components such as collagen and heparin and to specific cell surface receptors. The ligand may also be an oligopeptide, having from 3 to about 25 amino-acids, present in such natural proteins, such as the tripeptide RGD (arginine-glycine-aspartic acid), the tetrapeptide RGDS (meaning RGD-serine), the pentapeptide GRGDS or the like. RGD is found in the integrin-binding domains of a number of ligands, and sequences flanking this tripeptide are presumed to determine the exact binding specificity. For a better affinity with surrounding cells and a better compatibility with the other components of the formulations of this invention, the said ligand may further be chemically modified, for instance by the inclusion of unsaturated polymerizable groups, preferably of the same nature as the unsaturated end groups of the crosslinkable macromer, for instance by N-methacryloylation. In this case, the ligand can be covalently anchored onto the polymer matrix resulting from crosslinking of the functional prepolymer and will not be easily leachable, unless after degradation of the matrix. Such incorporated peptide sequences (optionally chemically modified) are also able to contribute to the angiogenesis process and to the cell ingrowth process and therefore lead to improved bone formation. The ligand may also be modified by incorporating it into a suitable biologically inert polymer material serving as a hydrophilic coating. An example of such a coating polymer material is poly-N-2-hydroxypropylmethacrylamide and related copolymers such as disclosed for instance in WO98/19710. The formulations of this invention may additionally include one or more biopolymers such as hyaluronic acid (a high molecular weight polymer of acetylglucosamine and glucuronic acid), chondrointinsulfate, dermatansulfate and the like. These biopolymers can again be chemically modified (such as previously mentioned for gelatine derivatives and for ligands), e.g. by reaction with (meth)acrylic anhydride and/or or with an azlactone, so that they will contain polymerizable side groups. During the crosslinking/hardening step of the composition of the invention, these biopolymers can then also be covalently anchored onto the biodegradable matrix. Preferably, the weight ratio ligand:prepolymer is in the range from 0.002:1 to 0.65:1, more preferably from 0.005:1 to 0.05:1. When the composition of the invention includes a porosity-inducing component, it is especially advantageous that the said porosity-inducing component and the biologically-active component (in particular the ligand) are so selected and/or in proportions such that as to provide a synergistic effect in bone reconstruction.

The formulations of this invention may additionally include one or more biocompatible unsaturated, preferably ethylenically unsaturated, functional monomers, more preferably functional acrylates and/or methacrylates such as hydroxyalkyl methacrylates (in paticular 2-hydroxyethyl methacrylate or hydroxypropyl methacrylate) or vinylphosphonic acid for the purpose of either further adapting the viscosity of the crosslinkable formulation to the specific need of the implant or further increasing the strength of the final crosslinked formulation by participating in the crosslinking process at moderate temperature together with the multifunctional macromer. The choice of suitable functional monomers for this purpose depends on the viscosity and crosslinkability of the formulation to be achieved and is well within the knowledge of those skilled in the art of acrylic monomer formulation. The amount of such unsaturated functional monomer to be incorporated into the formulation of the invention is an effective amount for performing the desired viscosity-adaptation or strength-increase.

Finally, the formulations of the present invention may additionally include one or more polymerization initiators able to polymerize the crosslinkable macromer under the influence of light and/or redox systems able to polymerize the crosslinkable macromer through radical initiation, possibly under the influence of temperature. When polymerization takes place under the influence of light, for instance light having a wavelength of at least about 300 nm, suitable polymerization photoinitiators include heterocyclic compounds, for instance xanthines, acridines, phenazines or thiazines, or phenone or quinone derivatives, e.g. camphorquinone and acetophenone. A preferred photoinitiator system for room temperature light polymerization of a macromer of the invention consists of a combination of camphorquinone and one or more tertiary amines such as phenylglycine. When polymerization takes place in the absence of light, a suitable redox system includes a peroxide (e.g. acetyl, benzoyl, cumyl or tert-butyl peroxides), a hydroperoxide (e.g. cumyl or tert-butyl hysroperoxides), a perester (e.g. tert-butyl perbenzoate), an acyl alkylsulfonyl peroxide, a dialkyl peroxydicarbonate, a diperoxyketal, a ketone peroxide or an azo compound (e.g. 2,2'-azobisisobutyronitrile), possibly in association with at least a compound such as N,N-dimethyltoluidine. Preference shall be given to redox systems which are able to polymerize the macromers of the invention at a temperature not above about 40° C. within a reasonable period of time suitable for implantation into a mammal. Possibly, a combination of a polymerization photoinitiator and a redox system can also be used, leading to a so-called "dual curing" system combining both polymerization mechanisms. The amount of polymerization initiator and/or redox system incorporated into the formulations of this invention is an effective amount for achieving macromer polymerization at the desired rate and is well known to those skilled in the art of light or radical polymerization methods.

The manufacture of the formulations of this invention shall be performed according to methods well known in the art, namely by efficiently mixing the various components of the formulation by suitable means, depending on the equipment available, for a sufficient period of time to achieve a substantially homogeneous mixture. In order to avoid premature polymerization of the formulation, it is usually advisable to incorporate the polymerization initiator and/or redox system only at the very end of the mixing procedure, i.e. shortly before using the formulation for implantation. For the obtention of an homogeneous mixture, it may be advisable to pre-mix some of the additives, such as for instance the therapeutic agent(s), the mineral delivery system and/or the porosity-inducing component, prior to their incorporation into the biodegradable crosslinkable prepolymer.

The present invention further provides therapeutically-active biodegradable implants manufactured by polymerizing a formulation (including a crosslinkable macromer) such as previously described. Biodegradation of the said implants occurs at the linkages between the different region(s) of the crosslinkable multifunctional macromer of the invention and results in non-toxic fragments that constitute safe chemical intermediates in the body of a mammal. For this reason, the present invention is useful for the preparation of load-bearing and non load-bearing implants such as bones, cartilage, vertebral discs, mandible prostheses and the like. Accordingly the invention also provides a method for preparing a therapeutically-active biodegradable implant including the steps of (a) combining a biodegradable crosslinkable prepolymer having at least two polymerizable end groups and optionally a hydrophilic sequence with one of a biologically-active ingredient, a mineral delivery system, a biocompatible unsaturated functional monomer, a biocompatible porosity-inducing component and/or a polymerization initiator, (b) implanting the said combination into the body of a mammal, such as a human, a horse, a dog, a bovine or the like at a place suitable for growth and (c) exposing the said implanted combination to conditions suitable for crosslinking the biodegradable crosslinkable multifunctional prepolymer at a temperature not exceeding about 40° C. The said method is widely applicable to a range of bone implants, as mentioned hereinabove. Namely, it is applicable to both load-bearing applications (such as for instance a hip implant) and non load-bearing applications (such as for instance a cronal fracture) for curing both self- and non self-healing bone defects.

Furthermore, the invention provides a method for repairing bone defects by implanting a bone repair formulation as previously described into the body of a mammal at a place suitable for bone growth (e.g. a bone cavity), and further crosslinking in situ the said bone repair formulation under the influence of light and/or a temperature not exceeding about 40° C. The detailed nature of the ingredients of the bone repair formulation is as disclosed in the previous part of this application. The crosslinking step of the bone defect repair method of the present invention may be carried out by any acceptable means known in the art, such as placing the bone site to be repaired, including the implanted bone repair formulation, in the presence of a device such as a lamp providing a light with a wavelength of at least about 300 nm or of a source of moderate heat (ensuring a temperature not exceeding about about 40° C.) for a period of time sufficient to achieve a substantially complete polymerization/crosslinking of the prepolymer. Completeness of polymerization can be monitored and followed by conventional means well known in the art such as, for instance, differential scanning calorimetry and/or rheometry. The success of the therapeutic implant and the corresponding bone defect repair will be evaluated and followed by suitable means well known in the art, such as macroscopic observation, scintigraphy and/or histology.

The present invention will now be explained in further details by reference to the following examples, which are provided for illustrative purposes only and without any limiting intention.

EXAMPLE 1

Preparation of a Polyester Bis-methacrylate a) Preparation of a Polyester Diol Prepolymer Equimolar amounts (0.05 mole) of recrystallized D,L-lactide (7.2 g) and distilled ε-caprolactone (5.7 g) was added into a polymerization tube. 0.005 mole of 1,6-hexanediol was then added to the mixture, together with 0.00917 g zinc acetate as a catalyst. The polymerization tube was then immersed into carbon dioxide ice at −78° C., evaucated and sealed while still under vacuum. Polymerization was then performed by placing the said tube into a thermostatic bath at 140° C. for 52 hours, thus resulting in 13.49 g of a poly(DL-lactide-co-ε-caprolactone)-co-hexanediol containing 0.005 alcohol end groups per macromolecule. This polymer was characterized using $^1$H- and $^{13}$C-NMR spectroscopy, differential scanning calorimetry and gel permeation chromatography, showing an average molecular weight of about 2,700.

b) Acrylation of the Polyester Diol

The polyester diol prepolymer obtained in example 1 was dissolved in 27 ml of freshly distilled methylene chloride. Then 2.3 g distilled methacrylic anhydride (0.015 mole) and 0.275 g dimethylaminopyridine were added and reaction was allowed to perform for 96 hours at room temperature, thus resulting in a poly(DL-lactide-co-ε-caprolactone)-co-hexanediol capped at both ends with methacrylate groups. This polymer was characterized using $^1$H- and $^{13}$C-NMR spectroscopy, differential scanning calorimetry and gel permeation chromatography.

EXAMPLE 2

Preparation of a Formulation for Bone Defect Repair 0.2546 g of the polyester bis-methacrylate obtained in example 1 was mixed together with 0.2562 g of demineralized bone powder, 4.42 mg of DL-camphoroquinone and 2.54 mg N-phenylglycine until a composite paste (with a viscosity such that it is deformable at moderate temperature by hand or by a syringe) is obtained (all components, except bone powder, being previously sterilized by means of ethylene oxide). This paste was then inserted into a cranial defect experimentally created in a dog. The animal study described herein was conducted according to methods approved by regulatory authorities. The composite was then crosslinked by exposure to visible light (blue light, maximum wavelength of 470 nm), using a dental lamp (Dental Visible Light Curing Unit, available from Minnesota Mining Company, United States) for a period of 20 seconds. In vivo histological evaluation of the defect repair was conducted three months after operation and is detailed in example 19 below.

EXAMPLE 3

Preparation of a Bismethacrylate Polyorthoester a) Preparation of Polyorthoester-diol While maintaining anhydrous conditions, 1,6-hexanediol (112.85 g, 0.955 mole) and 1.8 l of tetrahydrofuran (distilled over calcium hydride) were placed into a 5 l three-necked flask equipped with an overhead stirrer, an argon inlet tube and a condenser on a trap. The mixture was stirred until all solids have dissolved; then 3,9-bis(ethylidene 2,4,8,10-tetraoxaspiro[5,5]undecane) (182.44 g, 0.859 mole) is added. Polymerization was initiated by the addition of 0.5 ml of a 20 mg/ml solution of p-toluenesulfonic acid in tetrahydrofuran. The polymerization temperature rapidly rose to the boiling point of tetrahydrofuran and then gradually decreased. Stirring was continued for about 2 hours, then 1 ml of a triethylamine stabilizer was added and the reaction mixture very slowly poured with vigorous stirring into about 5 gallons of methanol containing 10 ml of triethylamine. The precipitated polymer was collected by vacuum filtration and dried in a vacuum oven at 60° C. for 24 hours, thus yielding 265 g (90%). A molecular weight of 3,500 was determined by gel permeation chromatography.

b) Preparation of a Bismethacrylate Polyorthoester

The polyorthoester (265 g) obtained in example 3-a was dissolved in dichloromethane (1.8 l, distilled over calcium hydride) in a 5 l two-neck flask. Triethylamine (6 g, 0.059 mole) was added, then methacryloyl chloride (10 g, 0.0956 mole) was added dropwise while keeping the reaction temperature at 0° C. The reaction mixture was stirred for 24 hours and the resulting polymer was washed with 0.1 M $H_2SO_4$, then extracted three times with an aqueous 8% $NaHCO_3$ solution and finally precipitated in methanol. The precipitated polymer was collected by filtration and dried at reduced pressure for 24 hours, yielding an amount of 258 g (96%).

EXAMPLE 4

Preparation of a Bismethacrylate Polyester

While maintaining anhydrous conditions, recrystallized D,L-lactide (0.7206 g, 0.005 mole) and 5 ml of tetrahydrofuran distilled over calcium hydride are placed into a 25 ml two-necked flask equipped with an argon inlet tube. The mixture was stirred until all D,L-lactide was dissolved. In another 25 ml two-necked flask equipped with a rubber septum, 1,6-hexanediol (0.0295 g, 0.00025 mole, previously dried at 60° C. at reduced pressure over $P_2O_5$) and a potassium tertiary butoxide initiator (0.0561 g, 0.0005 mole) were dissolved in 5 ml distilled tetrahydrofuran. This mixture was stirred for 15 minutes. The initiator solution was then injected into the monomer solution through the rubber septum by using a syringe. Polymerization was performed at room temperature and, after 5 minutes, was terminated by adding an excess of methacryloyl chloride (0.52 g, 0.005 mole). The resulting polymer solution was washed with a 1 M $H_2SO_4$ aqueous solution, extracted three times with a 8% $NaHCO_3$ aqueous solution, dried over $MgSO_4$, precipitated in pentane and dried under reduced pressure for 24 hours. 0.7684 g (98% yield) of a polyester-bismethacrylate was thus obtained. The polymer was characterized using $^1H$- and $^{13}C$-NMR spectroscopy, differential scanning calorimetry and gel permeation chromatography (showing an average molecular weight of 3,136).

EXAMPLE 5

Preparation of a Polyester-diol Containing a Poly (ethylene oxide) Sequence

Recrystallized D,L-lactide (0.1 mole, 14.41 g) was added into a polymerization tube. 5 g of a poly(ethylene oxide)-diol, (average molecular weight 1,000, 0.005 mole, previously dried at 60° C. under reduced pressure for 24 hours over $P_2O_5$) was added to the tube together with as a zinc acetate catalyst (0.0183 g, 0.0001 mole). The polymerization tube was then immersed into carbon dioxide ice at −78° C., evacuated and sealed under reduced pressure. Polymerization was then performed by placing this polymerization tube in a thermostatic bath at 140° C. for 52 hours, thus resulting in 19.41 grams of poly(D,L-lactide)-co-poly(ethylene oxide)-co-poly(D,L-lactide)-diol containing 0.01 mole (0.17 g) of alcohol end groups per macromolecule. The polymer was characterized using $^1H$- and $^{13}C$-NMR spectroscopy, differential scanning calorimetry and gel permeation chromatography, showing an average molecular weight of 3,880. The alcohol end groups of this polymer were then converted into methacrylate end groups according to the procedure described in example 1.

EXAMPLE 6

Preparation of a Bone Repair Formulation Containing a Methacrylamide Modified Gelatin 0.2546 g of the polyester bismethacrylate obtained in example 1 was mixed together with 0.2546 g of methacrylamide-modified gelatin particles (having a particle size in the range of 100 to 150 μm), 4.42 mg DL-camphorquinone and 2.54 mg N-phenylglycine until a composite paste (with a viscosity such that it is deformable at moderate temperature by hand or syringe) is obtained. The synthesis of a methacrylamide modified gelatin is described by A. Van Den Bulcke et al., *Biomacromolecules* (2000) 1:31–38. This paste is then injected in a cast and hardened/crosslinked by irradiation under the conditions of example 2.

EXAMPLE 7

Preparation of a Bone Repair Formulation Containing Calcium Phosphate Powder and Bone Morphogenetic Proteins 0.2546 g of the polyester methacrylate obtained in example 1 was mixed together with 0.2546 g of a calcium phosphate powder (having a particle size in the range of 100 to 150 μm), 4.42 mg DL-camphorquinone, 2.54 mg N-phenylglycine and 0.025 g of freeze dried gelatin powder (having a particle size in the range of 100 to 150 μm) containing 10 μg bone morphogenetic proteins, until a composite paste (with a viscosity such that it is deformable at moderate temperature by hand or syringe) is obtained. This paste is injected in a cast and hardened/crosslinked by irradiation under the same conditions as described in example 3.

EXAMPLE 8

Preparation of a Branched Polyester-tetrol Prepolymer

Equimolar amounts (0.05 mole) of recrystallized D,L-lactide (7.2 g) and distilled ε-caprolactone (5.7 g) were added into a polymerization tube. Pentaerythritol (0.005 mole, 0.6807 g, previously dried at 60° C. under reduced pressure for 24 hours over $P_2O_5$) was added to the tube together with a zinc acetate catalyst (0.0183 g, 0.0001 mole). The polymerization tube was then immersed into carbon dioxide ice at −78° C., evacuated and sealed under reduced pressure. Polymerization was then performed by placing this polymerization tube in a thermostatic bath at 140° C. for 52 hours, thus resulting in 13.58 g of a poly(D,L-lactide)-co-poly(ε-caprolactone)-pentaerythritol-tetrol containing 0.01 mole (0.17 g) of alcohol end groups per macromolecule. The polymer was characterized using $^1H$- and $^{13}C$-NMR spectroscopy, differential scanning calorimetry and gel permeation chromatography, showing an average molecular weight of 2,716.

The alcohol end groups of this branched polyester-tetrol may be converted into methacrylate end groups according to the procedure described in example 1.

EXAMPLE 9

Preparation of a Bifunctional poly(D,L-lactide-co-ε-caprolactone) Prepolymer

A functional poly(D,L-lactide$_{50}$-co-ε-caprolactone)-hexanediol$_{20/1}$-methacrylate prepolymer is prepared according to the procedure described in example 8, except that pentaerythritol is replaced by hexanediol.

EXAMPLE 10

Preparation of a Composite Containing a Porosigen

In order to obtain an interconnecting porous structure, a porosigen was incorporated into the crosslinkable prepolymer resulting, after hardening, in a composite material. Gelatin and polysaccharide particles are porosigens because they are easily dissolved in an aquous environment at 37° C.

a) Gelatin as a Porosigen 250 mg of medical grade gelatin microparticles (ranging from 100 μm to 300 μm in diameter) are homogeneously mixed with an equal amount of the methacrylate-functionalised polyester of example 1. Then 1.2 mg DL-camphorquinone and 1.1 mg N-phenylglycine were added and all components were mixed thoroughly until a homogeneous composite paste was obtained. This paste was injected in a cast and crosslinked (i.e. hardened) by irradiating the paste with blue light (maximum wave length: 470 nm) for 20 seconds, using a 3M Dental Visible Curing Unit. Porous samples were obtained by leaching out the medical grade gelatin microparticles in a phosphate buffer (pH 7.4 at 37° C.) for one week. Porosity was determined by comparing the density of the composites before and after leaching.

b) Dextrane and Lactose as Porosigens

As an alternative to the previous embodiment, the high molecular weight dextrane polysaccharide and the lactose disaccharide are also suitable as porosigens. The preparation of composites containing dextrane, respectively lactose particles, is analogous to example 10-a.

EXAMPLE 11

Preparation of a Composite Containing a Porosigen and a Functional Monomer 200 mg of the functional prepolymer of example 9 (1.4×10$^{-4}$ moles of methacrylate endgroups) was mixed with 36.4 mg hydroxyethylmethacrylate (2.8×10$^{-4}$ moles). 236.4 mg of a medical grade gelatin (particles sizes: 100 μm–140 μm) was added. Finally, the photoinitiator (1.4 mg DL-camphorquinone and 1.3 mg N-phenylglycine) was added into the mixture until a homogeneous curable composite was obtained. This paste was injected and crosslinked while using the method of example 10.

EXAMPLE 12

Preparation of a Composite Containing a Mineral Component Delivery System 250 mg of a powdery mineral component delivery system was mixed with 250 mg of the functional copolymer of example 9. Then 1.2 mg DL-camphorquinone and 1.1 mg N-phenylglycine were added and all components were mixed thoroughly untill a homogeneous composite paste was obtained. This paste was injected and crosslinked while using the method of example 10. Various powdery mineral components may be used in this embodiment, such as:
a) α-tricalciumphosphate
b) hydroxyapatite
c) octacalciumphosphate
d) calciumcarbonate
e) β-tricalcium phosphate.

EXAMPLE 13

Figure 3:
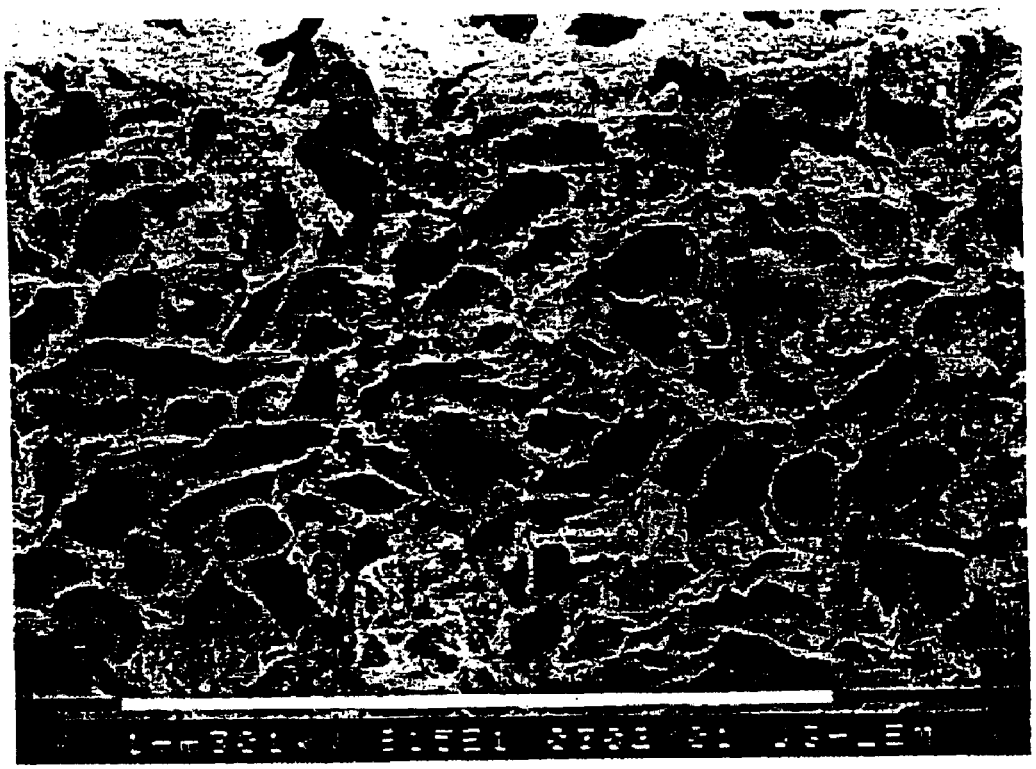
FIG. 3 represents the scanning electron miscroscopy image of a composite comprising gelatine, a mineral component delivery system and a crosslinked biodegradable polymer.
Figure 4:
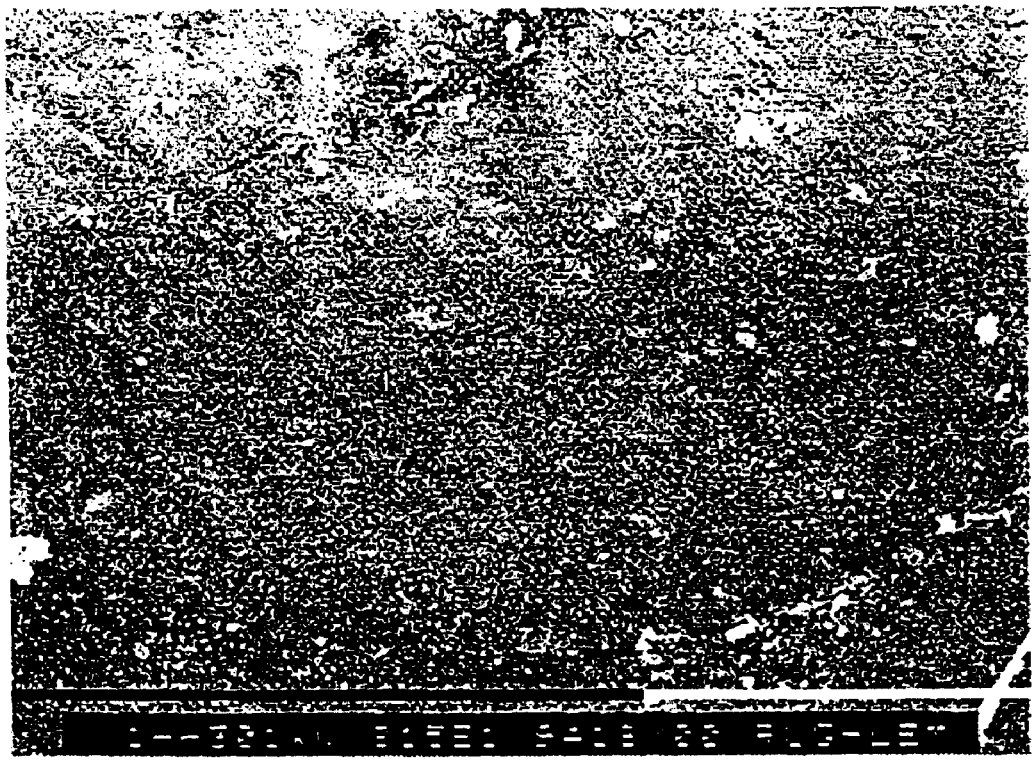
FIG. 4 represents the scanning electron miscroscopy image of a composite comprising a crosslinked biodegradable polymer alone.

Preparation of a Composite Containing a Porosity-inducing Component and a Mineral Component Delivery System 250 mg of a medical grade gelatin powder (particle diameter 100 μm–140 μm) was mixed with 125 mg α-tricalciumphosphate and 250 mg of the functional prepolymer of example 9. 1.2 mg DL-camphorquinone and 1.1 mg N-phenylglycine were added and all components were mixed thoroughly untill a homogeneous composite-paste was obtained. This paste was injected and crosslinked while using the method of example 10. FIG. 3 shows the scanning electron miscroscopy image (×81.5) of this composite after leaching in a phosphate buffer (pH 7.4 at 37° C.) for one week. For a purpose of comparison, FIG. 4 shows the scanning electron miscroscopy image (×81.5) of the composite obtained from crosslinking the functional prepolymer of example 9 alone after leaching under the same conditions.

EXAMPLE 14

Preparation of a Composite Containing a Porosity-inducing Component, a Mineral Component Delivery System and a Functional Monomer 300 mg of a medical grade gelatin powder (particle diameter 100 μm–140 μm) was mixed with 400 mg α-tricalciumphosphate, 250 mg of the functional prepolymer of example 9 and 45.6 mg hydroxyethylmethacrylate. 1.4 mg DL-camphorquinone and 1.3 mg N-phenylglycine were added and all components were mixed thoroughly untill a homogeneous composite paste was obtained. This paste was injected and crosslinked while using the method of example 10.

EXAMPLE 15

Preparation of a Composite Containing a Reactive Oligopeptide and a Porosigen a) Synthesis of a Reactive Oligopeptide α-hydroxy-ω-carbonic acid-poly(ethylene glycol) (0.5 g) (molecular weight 1,000) was reacted in 10 ml distilled methylene chloride with 5 ml 94% methacrylic anhydride, catalyzed by triethylamine (5 ml) and stabilized with 0.01 g phenothiazine at room temperature for 24 hours. After reaction, the excess of triethylamine and methacrylic anhydride was distilled off under vacuum. The resulting polymer was then precipitated in diethylether, filtrated and washed. $^1$H-NMR spectrum was performed in order to verify the complete conversion of alcohol groups into methacrylate end groups. Next, it was dissolved in 50 ml H$_2$O, twice extracted with ether and three times with 35 ml methylene chloride in order to remove the mixed anhydride. $^1$H-NMR spectrum was performed in order to verify the purity of the polymer.

Then the carbonic acid end group were converted into N-hydroxy-succinimidyl end group as follows: 250 mg of the α-methacryl-ω-carbonic acid poly(ethylene glycol) and 24 mg N-hydroxy succinimide were allowed to cool in 5 ml methylene chloride to 0° C. 1 ml of 3M dicyclohexylcarbodiimide was added dropwise into the solution. After 36 hours, the reaction was complete. Celite was added and the solution was filtrated and washed with 1 part methylene chloride and 2 parts of diethylether. The resulting polymer was then precipitated in 80 ml diethylether, filtrated and washed. $^1$H-NMR spectrum was performed in order to verify the purity of the polymer.

Finally, the succinimylated poly(ethylene glycol) was coupled to an oligopeptide, $NH_2$-GRGDS, which is a cell-adhesive ligand. 0.5 succinimylated poly(ethylene glycol) was dissolved in 10 ml distilled and dry dimethylformamide (DMF). A solution of $NH_2$-GRGDS (1.1 molar excess) in 5 ml dry DMF was added dropwise. The reaction was performed at room temperature for 48 hours and followed by chromatography using methylene chloride/methanol (90/10) as eluent. The resulting polymer was then precipitated in diethylether, filtrated and washed with ether. In order to purify the α-methacryl-ω-GRGDS-poly(ethylene glycol) from the unreacted $NH_2$-GRGDS, an extraction was performed in methylene chloride/water (5 times) and dried in vacuo. The coupling efficiency was investigated by $^1$H-NMR spectroscopy.

b) Preparation of a Composite Containing α-methacryl-ω-GRGDS-poly(ethylene glycol) and a Functional Monomer 200 mg of the functional prepolymer of example 9 ($1.4 \times 10^{-4}$ moles of methacrylate end groups) was mixed with 36.4 mg hydroxyethylmethacrylate ($2.8 \times 10^{-4}$ moles), 10 mg of the α-methacryl-ω-GRGDS-poly(ethylene glycol) of example 15-a, 236.4 mg of a medical grade gelatine (particle sizes 100 μm–140 μm) and the photoinitiator (1.4 mg DL-camphorquinone and 1.3 mg N-phenylglycine). All components were mixed untill a homogeneous curable composite paste was obtained. This paste was injected and crosslinked while using the method of example 10.

EXAMPLE 16

Preparation of a Composite Containing Fibronectine and a Porosigen 250 mg of a medical grade gelatin powder (particle diameter 100 μm–140 μm) was mixed with 125 mg fibronectine powder and 250 mg of the functional prepolymer of example 9. Then 1.2 mg DL-camphorquinone and 1.1 mg N-phenylglycine were added and all components were mixed thoroughly untill a homogeneous composite-paste was obtained. This paste was injected and crosslinked while using the method of example 10.

EXAMPLE 17

Preparation of a Composite Containing Vitronectine and a Porosigen

The procedure of example 16 was repeated except that fibronectine was replaced by an equal amount (125 mg) of vitronectine.

EXAMPLE 18

Preparation of a Composite Containing Methacrylamide-modified Vitronectine or Methacrylamide-modified Fibronectine Copolymerized with Methacrylamide-modified Gelatine a) Synthesis of a Methacrylamide-modified Vitronectine or Methacrylamide-modified Fibronectine 2 g of vitronectine was dissolved in 20 ml phosphate-buffer (pH 7.8) at 40° C. 0.2 ml methacrylic anhydride was added and the reaction mixture was stirred for one hour at 40° C. Then, the mixture was diluted with 20 ml water and purified by dialysis for one day, after which the reaction product was freeze-dried. A similar procedure may be used by replacing vitronectine with fibronectine.

b) Copolymerization of a Methacrylamide-modified Vitronectine or Methacrylamide-modified Fibronectine with Methacrylamide-modified Gelatine Methacrylamide-modified gelatine (1.5 g) and the methacrylamide-modified vitronectine or methacrylamide-modified fibronectine (0.5 g) of example 18-a were dissolved in 10 ml distilled water at 40° C. An Irgacure® ultraviolet polymerization photoinitiator (0.084 g) was added, then the warm solution was injected in a cast and polymerized by UV irradiation (365 nm, 10 mW/cm$^2$) during 30 minutes. The resulting copolymer was then freeze-dried and crushed into small particles using a mortar.

c) Preparation of the Composite 250 mg of the copolymer powder of example 18-b was mixed with 250 mg of the functional prepolymer of example 9. 1.2 mg DL-camphorquinone and 1.1 mg N-phenylglycine were added and all components were mixed thoroughly until a homogeneous composite-paste was obtained. This paste was injected and crosslinked while using the method of example 10.

EXAMPLE 19

In vivo Experiments

Composites used for this in vivo experiment are described in examples 2 (without gelatine) and 10-a (with gelatine) respectively. For this biological study, 4 non-self healing (critical sized) cranial defects were created in the skull of a beagle dog. The defects were 12 mm in diameter and approximately 5 mm in depth. Three defects were filled with the composite of example 2 and the fourth defect was filled with autologous bone as control defect. Histological results reveal that all defects were bridged and showed good vascularization. In FIGS. 1 (relating to the composite of example 10-a) and 2 (relating to the composite of example 2), the presence of blood vessels is indicated by the arrows. It is clear that less vesicles are formed for the implant not comprising gelatins.

Additional in vivo experiments on rabbits (cranial defects) using the composite of example 14 also showed good vascularization and bone formation.

EXAMPLE 20

Fixation of a Metal Dental Implant by a Curable Composite

Placing an implant immediately into a fresh extraction socket neutralizes the waiting time of 6 to 8 months. There is less burden on the patient because drilling is reduced to a minimum. Since most types of implants were designed to be placed into healed alveolar ridges, the combination of a screw implant and a bone graft is still needed to fill the gap between the implant and the socket. The bone graft provides initial stability to the implant which is placed 2–5 mm apically into the socket. The forces are greatest at the wider bucco-lingual (or—palatal) diameter around the neck. After teeth extraction a metal screw implant is placed immediately apically into the extraction socket. The void between the bone and the implant is firmly packed with the photocurable composite of example 13 containing the biodegradable polyester bismethacrylate, gelatine as a porosigen and α-tricalcium phosphate as internal buffering additive and mineral source for bone formation. The cured filling resists the forces on the implant that are mainly concentrated at the neck of the implant. It is also able to prevent ingrowth of soft tissue and hence secure rehabilitation.

EXAMPLE 21

Fixation of a Metal Dental Implant by a Combination of Synthetic Bone Allograft and a Curable Composite After teeth extraction a metal screw implant is placed immediately apically into the extraction socket. The void between the bone and the implant is firmly packed with a xenograft or allograft material, e.g. Bioplant HTR Synthetic Bone Allograft (a mixture of porous polymethacrylate spheres coated with poly-2-hydroxyethylmethacrylate and an outer layer of calcium hydroxide carbonate; commercially available from Bioplant Inc., United States). The photocurable composite of example 12-a (containing a biodegradable polyester bismethacrylate and α-tricalcium phosphate as internal buffering additive and mineral source for bone formation) is then placed on top of the allograft filling in order to provide, after photocuring, a rigid collar around the metal implant. This cured ring keeps the implant in place during the initial stage of bone formation around the implant, which at the lower part of the implant is promoted by the allograft. The cured ring around the neck of the implant resists the forces on the implant that are mainly concentrated at the neck of the implant and is able to prevent ingrowth of soft tissue and hence secure rehabilitation.

What is claimed is:

1. A composition suitable for preparing a biodegradable implant, comprising a crosslinkable multifunctional prepolymer, the number average molecular weight of the said crosslinkable multifunctional prepolymer being in the range of 150 to 20,000 whereby the said composition has a viscosity such that it is deformable at a temperature of 0° to 6° C. into a three-dimensional shape, the said crosslinkable muitifunctional prepolymer being crosslinkable within the said temperature range and comprising at least one biodegradable region selected from the group consisting of poly-α-hydroxyacids, polyesters, polyaminoacids, polyorthoesters and mixtures thereof, or polyacetals, and at least one polymerizable region having at least two polymerizable end groups, wherein the said composition further comprises a biocompatible unsaturated functional monomer end an effective amount of a mineral biologically-active component delivery system and/or an effective amount of a biocompatible degradable or water-soluble porosity-inducing component or porous polymethacrylate spheres.

2. A composition according to claim 1, wherein the said crosslinkable multifunctional prepolymer further comprises a hydrophilic region.

3. A composition according to claim 1, wherein the said crosslinkable multifunctional prepolymer further comprises a hydrophilic region being a polyethylene glycol or a copolymer of ethylene oxide and an alkylene oxide with a degree of polymerization in the range of 2 to 500.

4. A composition according to claim 1, wherein the biodegradable region of the crosslinkable multifunctional prepolymer is a predominantly amorphous region.

5. A composition according to claim 1, wherein the said biodegradable region of the said crosslinkable multifunctional prepolymer is a polyester sequence resulting from copolymerizing a mixture of lactones wherein none of the lactone comonomers is present in the resulting polyester sequence in a molar proportion above 75%.

6. A composition according to claim 1, wherein the polymerizable region of the said crosslinkable multifunctional prepolymer contains ethylenic and/or acetylenic unsaturations.

7. A composition according to claim 1, further comprising at least one additive selected from polymerization initiators including redox initiators or photoinitiators.

8. A composition according to claim 1, wherein the said mineral biologically-active component delivery system is selected from the group consisting of demineralized bone, resorbable calcium phosphate-based particles, hydroxyapatite, tricalcium phosphate, octacalcium phosphate, calcium carbonate, calcium sulfate and coral.

9. A composition according to claim 1, wherein the said mineral biologically-active component delivery system is present in an amount able to increase the pH within the degrading polymer.

10. A composition according to claim 1, wherein the weight ratio mineral system: prepolymer is in the range from 0.05:1 to 20:1.

11. A composition according to claim 1, wherein the said mineral biologically-active component delivery system is in the form of a powder.

12. A composition according to claim 1, wherein the said biocompatible degradable or water-soluble porosity-inducing component is selected from the group consisting of a monosaccharide, an oligosaccharide, a polysaccharide. gelatine, a crosslinked gelatine and a synthetic polymeric porous particle.

13. A composition according to claim 1, wherein the weight ratio porosity-inducing component: prepolymer is in the range from 0.05:1 to 20:1.

14. A composition according to claim 1, further comprising a biologically-active component selected from the group consisting of bone repair promoters, antimicrobial agents, proteins, peptides, hormones, carbohydrates, antineoplastic agents, antiangiogenic agents, vasoactive agents, anticoagulants, immunomodulators, cytotoxic agents, antiviral agents, antibodies, neurotransmitters, oligonucleotides, lipids, plasmids, DNA, diagnostic agents and ligands with affinity for cells.

15. A composition according to claim 1, further comprising a protein selected from the group consisting of fibronectin, vitronectin and oligopeptides having from 3 to 25 amino-acids.

16. A composition according to claim 1, wherein the said biocompatible degradable or water-soluble porosity-inducing component and the said biologically-active component are in proportions such that as to provide a synergistic effect in bone reconstruction.

17. A composition according to claim 1, wherein the said biocompatible unsaturated functional monomer is selected from the group consisting of functional acrylates and methacrylates, and vinylphosphonic acid.

18. A therapeutically-active biodegradable implant comprising the crosslinked product of a composition comprising a crosslinkable muitifunctional prepolymer, the number average molecular weight of the said crosslinkable multifunctional prepolymer being in the range of 150 to 20,000 whereby the said composition has a viscosity such that it is deformable at a temperature of 0° to 60° C. into a three-dimensional shape, the said crosslinkable multifunctional prepolymer being crosslinkable within the said temperature range and comprising at least one biodegradable region selected from the group consisting of poly-α-hydroxyacids, polyesters, polyaminoacids, polyorthoesters and mixtures thereof, or polyacetals, and at least one polymerizable region having at least two polymerizable end groups, wherein the said composition further comprises a biocompatible unsaturated functional monomer and an effective amount of a mineral biologically-active component delivery system and/or an effective amount of a biocompatible degradable or water-soluble porosity-inducing component or porous polymethacrylate spheres.

19. A therapeutically-active biodegradable implant according to claim 18, wherein the implant is a bone implant or a bone cement.

20. A therapeutically-active biodegradable implant according to claim 18, wherein the composition further comprises a biologically-active component selected from the group consisting of bone repair promoters, antimicrobial agents, proteins, peptides, hormones, carbohydrates, antineoplastic agents, antiangiogenic agents, vasoactive agents, anticoagulants, immunomodulators, cytotoxic agents, antiviral agents, antibodies, neurotransmitters, oligonucleotides, lipids, plasmids, DNA, diagnostic agents and ligands with affinity for cells.

21. A method for repairing a bone defect by implanting a bone repair low viscosity formulation into the body of a mammal at a place suitable for bone growth and further crosslinking the said formulation, wherein the said formulation comprises a composition comprising a crosslinkable multifunctional prepolymer, the number average molecular weight of the said crosslinkable muitifunctional prepolymer being in the range of 150 to 20,000 whereby the said composition has a viscosity such that it is deformable at a temperature of 0° to 60° C. into a three-dimensional shape, the said crosslinkable muitifunctional prepolymer being crosslinkable within the said temperature range and comprising at least one biodegradable region selected from the group consisting of poly-α-hydroxyacids, polyesters, polyaminoacids, polyorthoesters and mixtures thereof, or polyacetals, and at least one polymerizable region having at least two polymerizable end groups, wherein the said composition further comprises a biocompatible unsaturated functional monomer and an effective amount of a mineral biologically-active component delivery system and/or an effective amount of a biocompatible degradable or water-soluble porosity-inducing component or porous polymethacrylate spheres.

* * * * *

UNITED STATES PATENT AND TRADEMARK OFFICE
CERTIFICATE OF CORRECTION

PATENT NO. : 6,933,328 B2 Page 1 of 1
APPLICATION NO. : 10/239623
DATED : August 23, 2005
INVENTOR(S) : Etienne Honoré Schacht It is certified that error appears in the above-identified patent and that said Letters Patent is hereby corrected as shown below:

Claim 1, line 6, "6°C" should read -- 60°C --

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,933,328 B2 | Page 1 of 1 |
| APPLICATION NO. | : 10/239623 | |
| DATED | : August 23, 2005 | |
| INVENTOR(S) | : Etienne Honoré Schacht | |

It is certified that error appears in the above-identified patent and that said Letters Patent is hereby corrected as shown below:

Column 21, Claim 1, line 38, "6°C" should read -- 60°C --

This certificate supersedes the Certificate of Correction issued November 18, 2008.

Signed and Sealed this

Ninth Day of December, 2008

JON W. DUDAS
*Director of the United States Patent and Trademark Office*

UNITED STATES PATENT AND TRADEMARK OFFICE
Certificate

Patent No. 6,933,328 B2

Patented: August 23, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Etienne Honoré Schacht, Staden (BE); and Geert Jackers, Herzele (BE).

Signed and Sealed this Ninth Day of November 2010.

DAVID W. WU
*Supervisory Patent Examiner*
Art Unit 1796
Technology Center 1700